United States Patent
Link

(10) Patent No.: US 6,235,032 B1
(45) Date of Patent: May 22, 2001

(54) CALCANEAL BONE PLATE

(75) Inventor: Helmut D. Link, Hamburg (DE)

(73) Assignee: Waldemar Link (GmbH & Co), Hamburg (DE)

(*) Notice: Subject to any disclaimer, the term of this patent is extended or adjusted under 35 U.S.C. 154(b) by 0 days.

(21) Appl. No.: 09/269,691
(22) PCT Filed: Aug. 21, 1997
(86) PCT No.: PCT/EP97/04552
 § 371 Date: Jan. 11, 2000
 § 102(e) Date: Jan. 11, 2000
(87) PCT Pub. No.: WO98/07380
 PCT Pub. Date: Feb. 26, 1998

(30) Foreign Application Priority Data

Aug. 22, 1996 (DE) .............................................. 296 14 425

(51) Int. Cl.[7] .................................................. A61F 5/01
(52) U.S. Cl. ...................................................... 606/69
(58) Field of Search ................... 606/69, 70, 71

(56) References Cited

U.S. PATENT DOCUMENTS

| | | | |
|---|---|---|---|
| 4,573,458 | * | 3/1986 | Lower ..................... 606/69 |
| 4,867,144 | * | 9/1989 | Karas et al. ............ 606/69 |
| 5,015,248 | * | 5/1991 | Burstein et al. ........ 606/69 |
| 5,304,180 | * | 4/1994 | Slocum ................... 606/69 |
| 5,324,290 | * | 6/1994 | Zdeblick et al. ....... 606/69 |
| 5,718,705 | * | 2/1998 | Sammarco ............. 606/69 |
| 5,743,913 | * | 4/1998 | Wellisz .................. 606/69 |
| 5,797,916 | * | 8/1998 | McDowell .............. 606/69 |
| 5,931,839 | * | 8/1999 | Medoff ................... 606/69 |

\* cited by examiner

Primary Examiner—Paul J. Hirsch
(74) Attorney, Agent, or Firm—Morrison & Foerster LLP

(57) ABSTRACT

A bone plate for treating fractures of the calcaneal bone is characterized in that it is adapted to the physical shape of the bone surface and has compression screw bores (6). In a preferred embodiment, the bone plate has a T-shape, and transverse offset projections arranged at one end of a longitudinal portion with further transverse portions at the other end. The plate is arched along the center axis in a portion from halfway to two thirds of a distance from the first end to the second end, and the offset and transverse projections are arched about an axis running substantially parallel to the longitudinal portion.

5 Claims, 1 Drawing Sheet

CALCANEAL BONE PLATE

Figure 1:
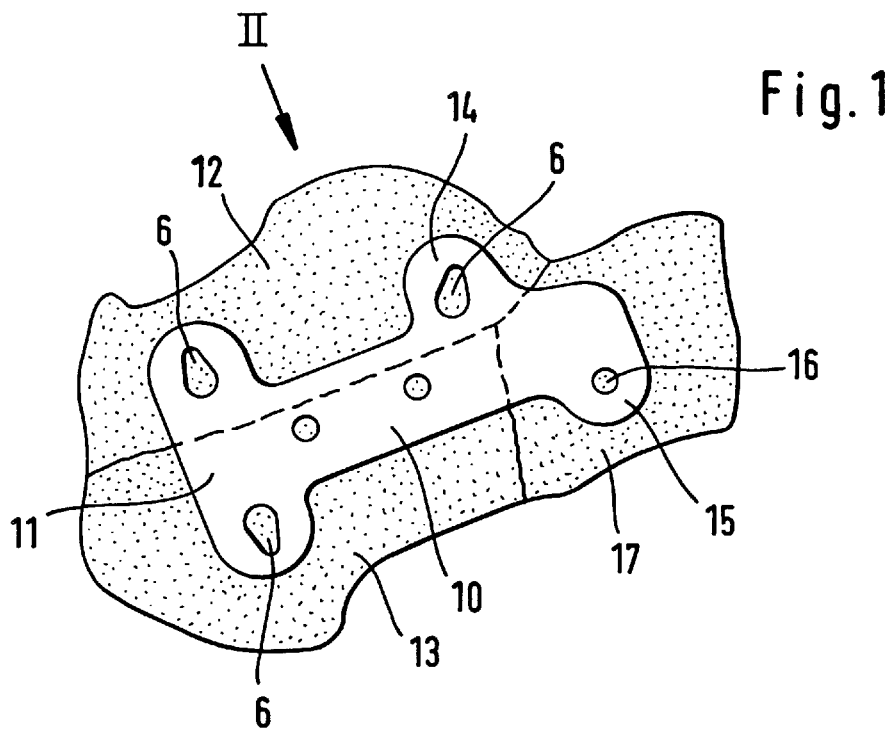

The invention relates to a bone plate for treating fractures of the calcaneal bone.

The complicated physical arrangement of the articular surfaces of the calcaneal bone makes it difficult to reposition these surfaces accurately following fractures. Persistent problems are relatively common (ZWIPP: Der intraartikuläre subthalamische Fersenbeinbruch [The intraarticular subthalamic fracture of the calcaneal bone], Operat. Orthopädie Traumatologie 7 (1995) 237 et seq.). To stabilize the repositioned fragments, use is mainly made of H-shaped and T-shaped plates which are flat and, if appropriate, are bent to shape in order to adapt to the physical surface shape of the bone (FR-A-2622431). This not only demands considerable manual dexterity but also requires that the operating surgeon has a detailed picture of the surface shape of the affected bone, although such a detailed picture can be obtained only with difficulty on account of the presence of the fragmented bone. Also, the available contours of the H-plates and T-plates in many cases fail to provide an adequate adaptation to the fracture pattern. An unsuitable choice or configuration of the plates in terms of their contour and their physical shape can therefore easily lead to incorrect results, which go unnoticed. It can also happen that insufficient healing is obtained as a result of the fracture gaps being too large.

The invention is based on the object of minimizing the aforementioned disadvantages. The solution according to the invention lies in the features of claim 1 and preferably those of the subclaims.

Although the calcaneal bone fractures which occur display a very wide variety (ZWIPP loc. cit.), certain typical fracture patterns can nevertheless be distinguished. The invention makes available a bone plate which is suitable for a common fracture pattern.

The bone plate according to the invention which is to be arranged laterally, and is particularly suited for so-called tongue fractures, has a longitudinal part with an approximately central arch, a transverse part projecting in both directions from the posterior end of the longitudinal part, and a first projection projecting downwards from the anterior end of the longitudinal part, and a second projection projecting cranially near this other end, and offset in relation to the first projection. The two projections are angled or arched in relation to one another (if appropriate including the longitudinal part) about an axis running approximately parallel to the longitudinal part, so that the longitudinal part located between them experiences an arching, and in particular the first projection is drawn inwards (for terminology see ZWIPP loc. cit. p 238). In tongue fractures, the transverse part located at the posterior end of the longitudinal part is suitable for drawing together the posterior facet fragment and the tuberous fragment located below this. The first projection can grip round the neck of the calcaneal bone in order to hold the anterior process, while the second projection below the posterior facet positions the posterior facet fragment or a further fragment located at this point.

The adaptation to physical surface shape of the bone concerns its lateral face between the calcaneal tuberosity and the anterior process. By means of the adaptation of the plate shape to the average surface configuration of the bone, it is possible, even when the individual bone shows certain deviations from the average shape, to exclude a grossly incorrect positioning of the fragments caused by the shape of the bone plate. In addition, in extreme cases, the operating surgeon is easily able to model the plate slightly, there being no . . . risk of gross mis-shaping because his corrections can be limited to slight changes of shape. The compressing effect of a number of screw bores ensures that the fragments are drawn together without gaps. This is known per se (DE-U-9217769).

When the compression bores at the ends of the transverse part are oriented towards one another, the posterior fragment and the tuberous facet fragment are drawn towards one another. If, on the second projection, there is a compression screw bore directed towards the longitudinal part, then the anterior area in particular of the posterior facet fragment is drawn towards the tuberous fragment. If the first projection has a compression screw bore directed towards the longitudinal part and to the transverse part, then the sustentacular fragment is drawn towards the two other said fragments.

Figure 2:
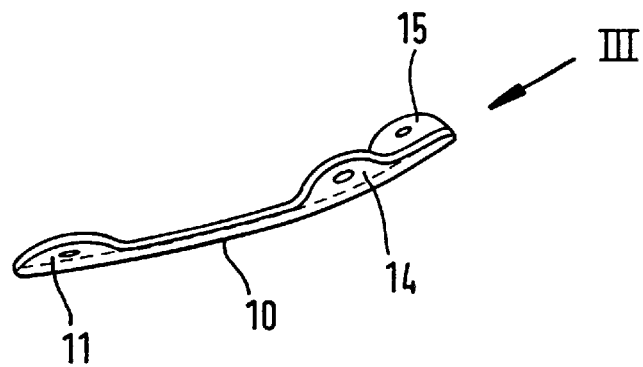
Figure 3:
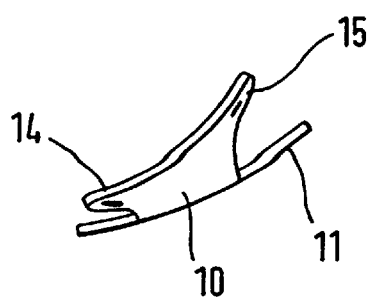

The invention is explained in greater detail hereinbelow, with reference to the drawing which shows advantageous illustrative embodiments. In the drawing:

FIG. 1 shows a side view of the calcaneal bone with the bone plate according to the invention, FIG. 2 shows a view of the bone plate shown in FIG. 1 in viewing direction II, and FIG. 3 shows a view of the bone plate in FIG. 1, in viewing direction III.

The bone plate shown in FIGS. 1 to 3 is intended for that type of fracture which is indicated in FIG. 1 by dashed lines between the upper or posterior facet fragment 12, the lower or tuberous fragment 13 and the sustentacular fragment 17. The posterior facet fragment 12 in particular can have further breaks or contusions. In FIG. 1, the right calcaneal bone is shown in a side view (posterior on the left side of the figure, anterior on the right).

The bone plate has a longitudinal part 10 at whose rear end a transverse part 11 is arranged somewhat in the shape of a T, which transverse part 11 protrudes beyond the longitudinal part 10 both above and below and contains compression screw bores 6 which are directed towards one another in order to connect an upper or posterior facet fragment 12 with a lower or tuberous fragment and to draw these fragments together. The longitudinal part 10 lies with its rear end at the lateral face of the calcaneal tuberosity and with its front end at the neck or at the lateral face of the anterior process. Protruding from near the front end of the longitudinal part 10 there is an upwardly directed projection 14 which is provided with a compression screw bore 6 and likewise engages the posterior facet fragment. Its centre distance from the front end is preferably 1–2 cm. Provided at the front end of the longitudinal part 10 there is a downward projection 15 whose screw bore 16 is used for securing the anterior process. Further screw bores can be distributed along the length of the longitudinal part 10.

The compression screw bore 6 contained in the upper projection 14 is directed downwards and slightly towards the rear.

The longitudinal part 10 is arched outwards in its central to forward third. In addition, its upper and lower projections 14, 15 are arched outwards about an axis running parallel to its longitudinal direction, so that the lower projection 15 can better engage round the neck of the calcaneal bone. They are also twisted slightly in relation to the rear transverse part 11, as FIG. 3 shows.

An advantage of this bone plate with its fairly short projections lies in the fact that although these projections are oriented in the direction towards adjacent articulation parts (e.g. talus), their short length ensures that they do not protrude harmfully into the articulation area.

What is claimed is:

1. A bone plate configured for treating fractures of the calcaneal bone comprising:

a longitudinal portion having a first end and a second end opposing the first end and having a center axis running from said first end to said second end, a first projection portion located at the second end and protruding in a first direction transverse to the center axis, a second projection portion located at the second end and offset in respect to the first projection portion and protruding transverse to the center axis in a direction away from the first projection, and transverse portions located at the first end and protruding in opposite directions transverse to the center axis, the transverse portions having screw bores formed therein, wherein the bone plate is arched along the center axis in a portion from halfway to two thirds of a distance from the first end to the second end, wherein the first and second projection portions are angled or arched relative to each other about an axis running substantially parallel to the center axis, and wherein at least one of the transverse portions, the first projection portions or the second projection portion has a compression type screw bore formed herein.

2. A bone plate according to claim 1, wherein the transverse portions are angled or arched relative to each other about the axis running approximately in parallel to the center axis.

3. A bone plate according to claim 1, wherein the transversal portions have compression type screw bores formed in at least end portions, wherein each screw bore has an axis and said axes of the screw bores converge.

4. A bone plate according to claim 1, wherein the second projection has a screw bore of the compression type, the screw bore having an axis oriented toward the center axis.

5. A bone plate according to claim 1, wherein the first projection has a screw bore of the compression type, the screw bore having an axis oriented toward the center axis.

\* \* \* \* \*